United States Patent [19]
Heeres et al.

[11] 3,991,201
[45] Nov. 9, 1976

[54] 1-(β-ARYL-β-R-ETHYL)IMIDAZOLES AS ANTIMICROBIAL AGENTS

[75] Inventors: Jan Heeres, Vosselaar; Leo J. J. Backx, Geel; Joseph H. Mostmans, Antwerp, all of Belgium

[73] Assignee: Janssen Pharmaceutica N.V., Beerse, Belgium

[22] Filed: May 19, 1975

[21] Appl. No.: 578,777

Related U.S. Application Data

[62] Division of Ser. No. 483,587, June 27, 1974, Pat. No. 3,927,017.

[52] U.S. Cl. .............................................. 424/273
[51] Int. Cl.² .......................................... A01N 9/22
[58] Field of Search ..................... 424/273; 210/309

[56] References Cited
FOREIGN PATENTS OR APPLICATIONS
1,487,326  5/1967  France ............................. 210/309

OTHER PUBLICATIONS
Chemical Abstracts, vol. 72 (1970), p. 90466v.
Chemical Abstracts, vol. 76 (1972), p. 3862n.

*Primary Examiner*—V. D. Turner
*Attorney, Agent, or Firm*—Salvatore R. Conte

[57] ABSTRACT

Compounds of the class of 1-(β-aryl-β-R-ethyl)imidazoles, useful as antibacterial and antifungal agents.

14 Claims, No Drawings

1-(β-ARYL-β-R-ETHYL)IMIDAZOLES AS ANTIMICROBIAL AGENTS

This is a division of Application Ser. No. 483,587 filed June 27, 1974, now U.S. Pat. No. 3,927,017, issued Dec. 16, 1975.

BACKGROUND OF THE INVENTION

In U.S. Pat. Nos. 3,658,813 and 3,717,655 there are described a number of antibacterial and antifungal 1-(β-aryl)-ethylimidazole ethers and amines. Among other differences the compounds of the present invention differ from those prior art compounds by the absence of an ether- or aminefunction at the β-position of the arylethyl chain.

DESCRIPTION OF THE PREFERRED EMBODIMENTS

This invention relates to a novel class of imidazole derivatives and more particularly to 1-(β-aryl-β-R-ethyl)imidazoles having the following formula:

(I)

wherein:
   Ar is a member selected from the group consisting of phenyl, mono-, di- and tri-halophenyl, loweralkylphenyl, loweralkyloxyphenyl, nitrophenyl, cyanophenyl and trifluoromethyl phenyl; and
   R is a member selected from the group consisting of alkyl, having from 1 to 10 carbons, cycloalkyl, lower alkenyl, aryl-lower alkyl and aryl-loweralkenyl, said aryl being a member selected from the group consisting of phenyl, mono-, di- and tri-halophenyl, loweralkylphenyl, loweralkyloxyphenyl, nitrophenyl, cyanophenyl and trifluoromethylphenyl.

The term "alkyl" as used in the foregoing definition of R is meant to include straight and branch chained aliphatic hydrocarbon radicals containing from 1 to about 10 carbons, such as, for example, methyl, ethyl, propyl, isopropyl, butyl, sec-pentyl, pentyl, hexyl, heptyl, octyl, decyl and the like.

"Lower alkyl", as used herein, refers to straight or branch chained alkyl radicals containing from 1 to about 6 carbons, such as, for example, methyl, ethyl, propyl, isopropyl, butyl, isobutyl, pentyl, hexyl, and the like.

"Lower alkenyl" refers to straight or branch chained unsaturated alkenyl radicals having from 3 to about 6 carbon atoms, preferably allyl.

The term "cycloalkyl" refers to cyclic hydrocarbon radicals having from 3 to 6 carbon atoms, such as cyclopropyl, cyclobutyl, cyclopentyl and cyclohexyl.

The term "halo" is generic to halogens of atomic weight less than 127, i.e., chloro, bromo, fluoro and iodo.

The therapeutically active acid addition salts of the foregoing compounds (I) are also embraced within the scope of this invention.

The compounds of formula (I) are conveniently prepared by N-alkylation of imidazole (II) with an appropriate reactive ester of formula (III) wherein Ar and R are as previously defined and wherein X is a reactive ester function, such as, for example, halo, mesyl, tosyl and the like, preferably mesyl.

The reaction is preferably carried out in an appropriate polar organic solvent, such as, for example, dimethylformamide, dimethylacetamide, benzonitrile, higher boiling alcohols such as butanol, and the like.

In order to enhance the rate of the reaction the use of somewhat elevated temperatures is appropriate and most conveniently the reaction is carried out at the reflux temperature of the reaction mixture.

In certain circumstances it is advantageous to add to the reaction mixture a small amount of an iodide salt, preferably an alkali metal iodide such as sodium- or potassium iodide.

The imidazole compound (I) is easily recovered from the reaction mixture according to conventional isolation procedures either as the free base, or, if so desired, in the form of an acid addition salt by treatment of the base with a suitable acid.

The reactive ester intermediates of formula (III) are generally prepared by converting the corresponding alcohol (IV) into the desired reactive ester according to methodologies generally known in the art.

For example, mesylates and tosylates are easily obtained by treating the alcohol with methanesulfonyl chloride or p-toluenesulfonyl chloride respectively, in the presence of an appropriate acid acceptor, such as, for example, pyridine.

Halides may be obtained by treating the alcohol with an appropriate halogenating agent, such as, for example, phosphorus pentachloride, phosphorus tribromide etc.

$$HO-CH_2-CH-R \longrightarrow \quad (III)$$
$$\quad\quad\quad\quad | $$
$$\quad\quad\quad AR$$
$$(IV)$$

The intermediate alcohols of formula (IV), a number of which are known compounds, may be prepared according to known procedures, such as, for example, the following:

An appropriately substituted arylacetonitrile of formula (V) is alkylated with an appropriate reactive ester RX (VI). Said alkylation reaction is preferably carried out by contacting first the arylacetonitrile with an appropriate strong base, such as, for example, sodium hydride, and thereafter adding the reactive ester to the reaction mixture. Suitable solvents for this reaction include amides such as dimethylformamide, dimethylacetamide and hexamethylphosphoric triamide, other common polar solvents such as dimethylsulfoxide, or mixtures of such solvents with, for example, an aromatic hydrocarbon, such as, benzene.

The substituted arylacetonitrile (VII) obtained in the foregoing step is then converted into an alkylester (VIII) of the corresponding arylacetic acid. This nitrile-to-ester conversion may be achieved in one step, for example, by heating the nitrile in an appropriate alcohol, or a mixture of an alcohol with an appropriate reaction inert organic solvent, such as, diisopropylether, in the presence of a strong inorganic acid such as, for example, hydrochloric acid. Alternatively the nitrile may be first hydrolyzed to the corresponding free arylacetic acid in the usual manner, e.g. with sodium hydroxide in ethyleneglycol, and said acid may thereafter be converted into the desired ester thereof by classical means.

The esters (VIII) may also be obtained by alkylating an appropriate alkyl arylacetate (IX) with RX according to known procedures.

The alcohols (IV) are then obtained after reduction of (VIII) with an appropriate reducing agent such as, for example, lithium aluminiumhydride, lithium borohydride, or sodium borohydride in the presence of a lithiumsalt, preferably a halide such as lithium iodide or lithium chloride.

The foregoing reactions are illustrated in the following schematic representation:

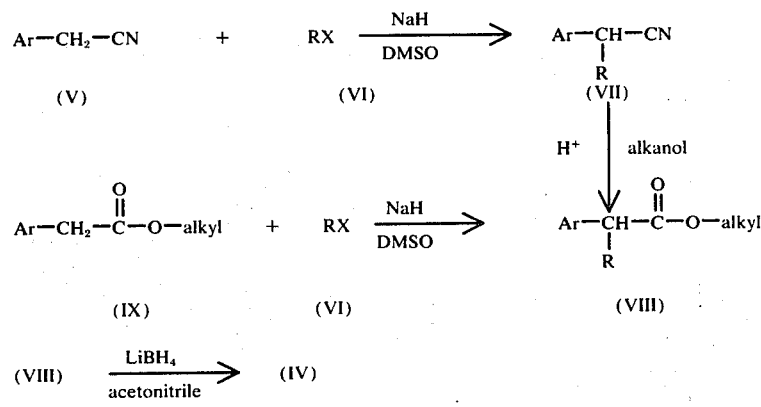

Due to the presence of an asymmetric carbon in the subject compounds (I), it is evident that their existence in the form of stereochemical optical isomers (enantiomers) is possible. If desired, the resolution and isolation or the production of a particular form can be accomplished by application of the general principles known in the art. Said enantiomers are naturally intended to be included within the scope of this invention.

Depending upon the conditions employed during the course of the reactions, the novel compounds herein are obtained either in the form of the free bases or salts thereof. The salts are converted to the free bases in the usual manner, e.g., by reaction with alkali such as sodium or potassium hydroxide. The compounds in base form may be converted to their therapeutically useful acid addition salts by reaction with an appropriate acid, as, for example, an inorganic acid such as hydrohalic acid, i.e., hydrochloric, hydrobromic or hydroiodic acid; sulfuric, nitric or thiocyanic acid; a phosphoric acid; an organic acid such as acetic, propionic, glycolic, lactic, pyruvic, oxalic, malonic, succinic, maleic, fumaric, malic, tartaric, citric, benzoic, cinnamic, mandelic, methanesulfonic, ethanesulfonic, hydroxyethanesulfonic, p-toluenesulfonic, salicylic, p-aminosalicylic, 2-phenoxybenzoic or 2-acetoxybenzoic acid.

The subject compound of formula (I) and the acid addition salts thereof are useful in combating fungi and bacteria as demonstrated by their broad spectrum of antifungal and antibacterial activity, particularly, against gram positive bacteria. The data given in the following tables illustrate such activity. The compounds in the tables are not listed for purposes of limiting the invention thereto, but only in order to exemplify the useful properties of all the compounds within the scope of formula (I).

The test for antifungal activity was performed using Sabouraud's liquid medium in test tubes each containing 4.5 ml of liquid medium, autoclaved at 120° C for 15 minutes. The compounds to be tested were dissolved in 50% ethanol at a concentration of 20 mg/ml and subsequently diluted with sterile distilled water to a concentration of 10 mg/ml. Successive decimal dilutions were then made with distilled water to give a series of stock solutions. To each tube containing 4.5 ml of Sabouraud's liquid medium was added 0.5 ml of one of the stock solutions to give a concentration of the compound under investigation of 100 $\mu$g, 10 $\mu$g, 1 $\mu$g or 0.1 $\mu$g per ml of medium.

Filamentous fungi were incubated at 25° C for 2 – 3 weeks. A square block of side 2 mm. was excised and inoculated into the liquid medium. A three-day old culture on Sabouraud's liquid medium was used for yeasts, and the inoculum was 0.05 ml per tube.

All the cultures were incubated at 25° C for 14 days. The final readings were taken after 2 weeks and are summarized in the Table A as follows:

| | |
|---|---|
| ++++ | = complete inhibition of growth at 0.1 $\mu$g/ml |
| +++ | = complete inhibition of growth at 1 $\mu$g/ml |
| ++ | = complete inhibition of growth at 10 $\mu$g/ml |
| + | = complete inhibition of growth of 100 $\mu$g/ml |
| 0 | = no effect, i.e. growth was observed at the highest concentration tested (100 $\mu$g/ml). |

The compounds under investigation were tested against the following 11 fungi:
1. *Microsporum canis* (*M.c.* in the table)
2. *Ctenomyces mentagrophytes* (*Ct.m.* in the table)
3. *Trichophyton rubrum* (*Tr.r.* in the table)
4. *Phialophora ver ucosa* (*Ph.v.* in the table)
5. *Cryptococcus neoformans* (*Cr.n.* in the table)
6. *Candida tropicalis* (*C.tr.* in the table)
7. *Candida albicans* (*C. alb.* in the table)

8. *Mucor* species (*Muc.* in the table)
9. *Aspergillus fumigatus* (*A.f.* in the table)
10. *Sporotrichum schenckii* (*Sp.s.* in the table)
11. *Saprolegnia* species (*Sap.* in the table)

Bactericidal tests were performed on cultures on phenol red dextrose broth Difco medium. The same decimal dilution techniques as described herebefore were used. The inoculum consisted of a platinum loop (5 mm diameter) from a 24 hour broth culture. 48 hours after incubation, subcultures were made from each culture and for the assessment of the bactericidal activity of the drugs under investigation the presence or absence of growth after 7 days incubation was scored as described above.

The subject compounds were tested against the following gram-positive bacilli and cocci:
1. *Erysipelothrix insidiosa* (*E. ins.* in the table),
2. *Staphylococcus hemolyticus* (*Staph.* in the table), and
3. *Streptococcus pyogenes* (*Strept.* in the table).

The results are summarized in Table B.

Table A

ANTIFUNGAL ACTIVITY

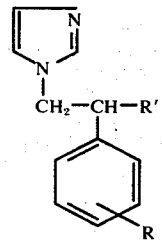

| R | R' | M.c. (1) | Ct.m. (2) | Tr.r (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|
| 4-F | —CH₃ | + | ++ | + | + | + | o | o | o | + | + | + |
| 4-Cl | —CH₃ | + | ++ | + | + | ++ | o | o | o | + | + | o |
| 2-Cl | —CH₂—CH=CH₂ | ++ | ++++ | ++++ | + | + | o | o | o | ++ | + | + |
| 2-Cl | —nC₃H₇ | ++++ | ++++ | ++++ | + | + | o | o | o | ++ | + | ++ |
| 2-Cl | —nC₅H₁₁ | ++ | ++++ | ++++ | + | ++ | + | o | o | ++ | ++ | + |
| 2-Cl | —nC₄H₉ | ++++ | ++++ | ++++ | + | + | + | + | o | ++ | ++ | ++ |
| 2-Cl | —CH₂—CH(CH₃)—CH₃ | ++ | ++++ | ++++ | + | ++ | o | o | o | ++ | ++ | + |
| 2,4-(Cl)₂ | —C₂H₅ | ++ | ++++ | ++++ | ++ | ++++ | + | + | + | ++++ | ++ | ++ |
| 2,4-(Cl)₂ | —nC₃H₇ | ++++ | ++++ | ++++ | ++ | ++++ | + | o | o | ++ | ++ | ++++ |
| 2,4-(Cl)₂ | —nC₄H₉ | ++++ | ++++ | ++++ | ++ | ++++ | ++ | ++ | o | ++ | ++ | ++ |
| 2,4-(Cl)₂ | —nC₅H₁₁ | ++ | ++++ | ++ | ++ | ++++ | + | ++ | + | ++ | ++ | ++ |
| 2,4-(Cl)₂ | —nC₇N₁₅ | ++ | ++++ | ++++ | + | ++++ | o | ++ | + | + | ++ | ++ |
| 2,4-(Cl)₂ | —nC₆H₁₃ | ++ | ++++ | ++++ | ++ | ++++ | ++ | ++ | ++ | + | ++++ | |
| 2,4-(Cl)₂ | —nC₈H₁₇ | ++ | ++++ | ++++ | + | ++++ | o | ++ | ++ | + | ++ | ++ |
| 2,4-(Cl)₂ | —CH₂—CH(CH₃)—CH₃ | ++ | ++++ | ++++ | + | ++++ | + | + | + | ++ | ++ | ++ |
| 4-F | —nC₃H₇ | ++ | ++++ | ++ | + | ++ | o | o | + | ++ | + | + |
| 4-F | —nC₅H₁₁ | + | ++++ | ++ | + | ++++ | o | + | + | + | + | + |
| 4-F | —nC₄H₉ | ++ | ++++ | ++++ | + | ++++ | o | + | ++ | ++ | ++ | ++ |
| 2,4-(Cl)₂ | —CH₂—CH₂—C₆H₅ | ++ | ++++ | ++++ | ++ | ++++ | o | + | + | + | +++ | +++ |
| 2,4-(Cl)₂ | —CH₂—CH=CH—(2-Cl-C₆H₄) | ++ | ++++ | ++++ | + | ++++ | o | + | + | o | ++++ | + |
| 2-Cl | —CH₂—CH=CH—(2-Cl-C₆H₄) | ++ | ++++ | ++++ | + | ++++ | o | + | + | + | ++ | + |

Table A-continued
ANTIFUNGAL ACTIVITY

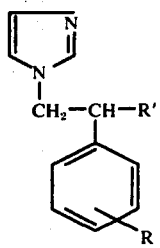

| R | R' | M.c. (1) | Ct.m. (2) | Tr.r (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|
| 2,4-(Cl)₂ | —CH₂—C₆H₄—Cl | ++ | ++++ | ++++ | + | ++++ | + | + | + | + | ++ | ++++ |
| 2,4-(Cl)₂ | —CH₂—C₆H₃Cl₂ (2,4) | ++ | ++++ | ++++ | + | ++++ | ++ | ++ | + | + | ++++ | + |
| 2,4-(Cl)₂ | —CH₂—C₆H₃Cl₂ (2,3) | ++ | ++++ | ++++ | + | ++++ | + | + | + | + | ++++ | + |
| 4-Cl | —CH₂—C₆H₄—Cl | ++ | ++++ | ++++ | + | ++++ | ++ | o | + | + | ++ | + |
| 4-Cl | —CH₂—C₆H₃Cl₂ | ++ | ++++ | ++++ | + | ++++ | + | + | + | + | ++ | + |
| 4-Cl | —CH₂—C₆H₄—Cl | ++ | ++++ | ++++ | + | ++++ | + | + | ++ | + | + | + |
| 4-Cl | —CH₂—C₆H₃Cl₂ | ++ | ++++ | ++ | + | ++++ | o | o | ++ | + | ++ | + |
| 2,6-(Cl)₂ | —CH₂—C₆H₄—Cl | ++++ | ++++ | ++++ | + | + | o | + | o | + | + | + |
| 2,6-(Cl)₂ | —CH₂—C₆H₃Cl₂ | ++ | ++ | ++++ | o | ++ | o | o | + | + | ++ | + |
| 2-Cl | —CH₂—C₆H₃Cl₂ | ++ | ++++ | ++++ | + | ++++ | o | + | + | + | ++ | |
| 2-Cl | —CH₂—C₆H₄—Cl | ++ | ++++ | ++++ | + | ++++ | o | ++ | + | + | ++ | + |
| 2,4-(Cl)₂ | —CH₂—C₆H₄—Cl | ++ | ++++ | ++++ | ++ | ++++ | ++++ | + | + | + | ++++ | ++ |
| 2-Cl | —CH₂—C₆H₄—Cl | ++ | ++++ | ++++ | + | ++++ | o | + | + | ++ | ++ | + |

Table A-continued

ANTIFUNGAL ACTIVITY

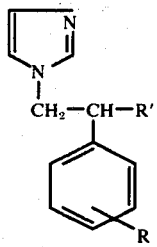

| R | R' | M.c. (1) | Ct.m. (2) | Tr.r (3) | Ph.v. (4) | Cr.n. (5) | C.tr. (6) | C.alb. (7) | Muc. (8) | A.f. (9) | Sp.s. (10) | Sap. (11) |
|---|---|---|---|---|---|---|---|---|---|---|---|---|
| 2,4-(Cl)$_2$ | -CH$_2$-C$_6$H$_4$-Br (2-Br) | ++ | ++++ | ++++ | ++ | ++++ | ++ | ++ | + | ++ | ++ | + |
| 2,4-(Cl)$_2$ | -CH$_2$-C$_6$H$_4$-Br (4-Br) | ++ | ++++ | ++++ | ++ | ++++ | ++ | ++ | ++ | + | ++ | + |
| H | cyclohexyl | ++ | ++++ | ++ | + | ++ | o | + | o | + | ++ | + |
| 2,4-(Cl)$_2$ | -CH$_2$-CH=CH$_2$ | +++ | +++ | +++ | +++ | +++ | + | + | o | +++ | +++ | +++ |
| 2,4-(Cl)$_2$ | -CH(CH$_3$)-CH$_2$-CH$_3$ | +++ | +++ | +++ | +++ | +++ | +++ | + | + | +++ | + | +++ |
| 4-F | -nC$_6$H$_{13}$ | +++ | +++ | +++ | + | +++ | + | + | + | + | ++ | + |
| 4-Cl | -nC$_3$H$_7$ | ++ | ++++ | ++++ | + | ++ | o | + | + | +++ | + | + |
| 4-F | -nC$_7$H$_{15}$ | ++ | ++ | ++++ | + | ++++ | o | ++ | + | + | ++ | + |
| 4-Cl | -nC$_4$H$_9$ | ++ | ++++ | ++++ | + | ++++ | ++ | + | + | ++ | ++ | + |
| 4-F | -nC$_8$H$_{17}$ | ++ | ++++ | ++++ | ++ | ++++ | o | ++ | ++ | + | ++ | ++ |
| 4-Cl | -nC$_5$H$_{11}$ | ++ | ++++ | ++++ | + | +++ | o | + | + | + | ++ | + |
| 4-Cl | -nC$_6$H$_{13}$ | ++ | ++++ | ++++ | + | ++++ | o | + | ++ | + | ++ | + |
| 2,4-(Cl)$_2$ | cyclohexyl | ++++ | ++++ | ++++ | + | ++++ | + | o | ++ | ++ | ++++ | |
| 2-Cl | -nC$_6$H$_{13}$ | ++ | ++++ | ++++ | + | ++++ | o | ++ | ++ | ++ | ++++ | ++ |
| 2,4-(Cl)$_2$ | cyclopentyl | ++++ | ++++ | ++++ | ++ | ++ | ++ | + | + | ++++ | ++++ | ++ |
| 2-Cl | -nC$_7$H$_{15}$ | ++ | ++++ | ++++ | + | ++ | o | + | ++ | + | ++++ | ++ |
| 2-Cl | -nC$_8$H$_{17}$ | ++ | ++++ | ++++ | + | ++ | o | ++ | + | + | ++++ | ++ |
| 2,4-(Cl)$_2$ | -CH$_2$-C$_6$H$_4$-OCH$_3$ | + | ++++ | ++++ | ++ | ++++ | ++ | ++ | ++ | + | ++ | + |
| H | -CH$_2$-C$_6$H$_3$(Cl)$_2$ (2,4-Cl$_2$) | ++ | ++++ | ++++ | ++ | ++++ | ++ | + | + | + | ++ | ++ |
| 2,4-(Cl)$_2$ | -CH$_2$-C$_6$H$_4$-CH$_3$ | ++ | ++++ | ++++ | + | ++++ | ++ | ++ | + | o | ++ | + |
| H | -CH$_2$-C$_6$H$_4$-Cl | + | ++ | ++ | + | ++ | + | + | + | + | + | + |

Table B

BACTERIOSTATIC AND BACTERIOCIDAL ACTIVITY

The table summarizes the activity against the gram-positive bacteria.

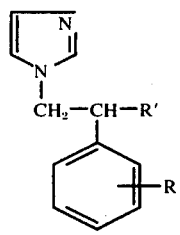

| R | R' | bacteriostatic activity | | | bacteriocidal activity | | |
|---|---|---|---|---|---|---|---|
| | | E. ins. | Staph. | Strept. | E. ins. | Staph. | Strept. |
| 4-F | —$CH_3$ | + | o | + | (+) | o | (+) |
| 4-Cl | —$CH_3$ | + | o | ++ | + | o | + |
| 2-Cl | —$CH_2$—$CH$=$CH_2$ | + | + | + | (+) | + | + |
| 2-Cl | —$nC_3H_7$ | ++ | o | + | + | o | + |
| 2-Cl | —$nC_5H_{11}$ | +++ | + | +++ | + | + | + |
| 2-Cl | —$nC_4H_9$ | ++ | + | ++ | ++ | + | ++ |
| 2-Cl | —$CH_2$—$CH(CH_3)$—$CH_3$ | ++ | + | ++ | ++ | + | ++ |
| 2,4-$(Cl)_2$ | —$C_2H_5$ | ++ | o | ++ | ++ | o | ++ |
| 2,4-$(Cl)_2$ | —$nC_3H_7$ | ++++ | ++ | ++++ | ++++ | + | ++++ |
| 2,4-$(Cl)_2$ | —$nC_4H_9$ | ++++ | ++ | ++++ | ++++ | + | ++++ |
| 2,4-$(Cl)_2$ | —$nC_5H_{11}$ | ++++ | +++ | ++++ | ++++ | ++ | ++++ |
| 2,4-$(Cl)_2$ | —$nC_7H_{15}$ | ++++ | +++ | ++++ | ++++ | ++ | ++++ |
| 2,4-$(Cl)_2$ | —$nC_6H_{13}$ | ++++ | +++ | ++++ | ++++ | ++ | ++++ |
| 2,4-$(Cl)_2$ | —$C_8H_{17}$ | ++++ | ++ | ++++ | ++++ | ++ | ++++ |
| 2,4-$(Cl)_2$ | —$CH_2$—$CH(CH_3)$—$CH_3$ | +++ | + | ++++ | ++ | + | ++++ |
| 4-F | —$nC_3H_7$ | ++ | o | ++ | + | o | ++ |
| 4-F | —$nC_5H_{11}$ | ++++ | ++ | ++++ | ++++ | + | ++++ |
| 4-F | —$nC_4H_9$ | ++ | + | ++ | + | o | + |
| 2,4-$(Cl)_2$ | —$CH_2$—$CH_2$—$C_6H_5$ | ++++ | +++ | ++++ | ++++ | ++ | ++++ |
| 2,4-$(Cl)_2$ | —$CH_2$—$CH$=$CH$—(2-Cl-$C_6H_4$) | +++ | +++ | ++++ | ++ | ++ | ++++ |
| 2-Cl | —$CH_2$—$CH$=$CH$—(2-Cl-$C_6H_4$) | +++ | ++ | +++ | ++ | + | ++ |
| 2,4-$(Cl)_2$ | —$CH_2$—(4-Cl-$C_6H_4$) | ++++ | ++ | ++++ | ++++ | ++ | ++++ |
| 2,4-$(Cl)_2$ | —$CH_2$—(3,4-$Cl_2$-$C_6H_3$) | ++++ | ++ | ++++ | ++++ | + | ++++ |

Table B-continued

BACTERIOSTATIC AND BACTERIOCIDAL ACTIVITY

The table summarizes the activity against the gram-positive bacteria.

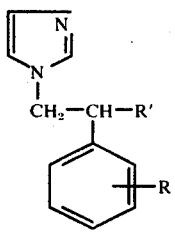

| R | R' | bacteriostatic activity | | | bacteriocidal activity | | |
|---|---|---|---|---|---|---|---|
| | | E. ins. | Staph. | Strept. | E. ins. | Staph. | Strept. |
| 2,4-(Cl)$_2$ | -CH$_2$-C$_6$H$_3$(Cl)(Cl) (2,3-diCl) | +++ | + | +++ | ++ | + | ++ |
| 4-Cl | -CH$_2$-C$_6$H$_4$-Cl (4-Cl) | ++ | + | ++ | ++ | + | ++ |
| 4-Cl | -CH$_2$-C$_6$H$_3$(Cl)(Cl) (3,4-diCl) | ++++ | ++ | +++ | ++++ | ++ | ++ |
| 4-Cl | -CH$_2$-C$_6$H$_4$-Cl (2-Cl) | +++ | ++ | ++ | ++ | + | ++ |
| 4-Cl | -CH$_2$-C$_6$H$_3$(Cl)(Cl) (2,3-diCl) | ++++ | ++ | ++++ | ++++ | + | ++++ |
| 2,6-(Cl)$_2$ | -CH$_2$-C$_6$H$_4$-Cl (4-Cl) | ++++ | + | ++++ | ++++ | + | ++++ |
| 2,6-(Cl)$_2$ | -CH$_2$-C$_6$H$_3$(Cl)(Cl) (3,4-diCl) | +++ | ++ | ++++ | ++ | ++ | ++++ |
| 2-Cl | -CH$_2$-C$_6$H$_3$(Cl)(Cl) (3,4-diCl) | ++ | + | ++++ | ++ | + | ++++ |
| 2-Cl | -CH$_2$-C$_6$H$_4$-Cl (4-Cl) | +++ | + | +++ | + | + | + |
| 2,4-(Cl)$_2$ | -CH$_2$-C$_6$H$_4$-Cl (2-Cl) | ++++ | ++ | ++++ | ++++ | o | ++++ |
| 2-Cl | -CH$_2$-C$_6$H$_4$-Cl (2-Cl) | +++ | + | ++++ | ++ | + | ++++ |
| 2,4-(Cl)$_2$ | -CH$_2$-C$_6$H$_4$-Br (2-Br) | +++ | ++ | ++++ | ++ | + | ++++ |

Table B-continued

BACTERIOSTATIC AND BACTERIOCIDAL ACTIVITY

The table summarizes the activity against the gram-positive bacteria.

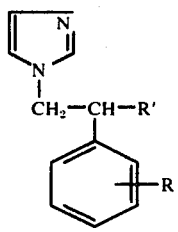

| R | R' | bacteriostatic activity E. ins. | Staph. | Strept. | bacteriocidal activity E. ins. | Staph. | Strept. |
|---|---|---|---|---|---|---|---|
| 2,4-(Cl)$_2$ | —CH$_2$—C$_6$H$_4$—Br | ++++ | ++ | ++++ | ++++ | ++ | ++++ |
| H | —C$_6$H$_{11}$ | ++++ | ++ | ++++ | ++++ | + | ++++ |
| 2,4-(Cl)$_2$ | —CH$_2$—CH=CH$_2$ | +++ | + | +++ | +++ | + | +++ |
| 2,4-(Cl)$_2$ | —CH(CH$_3$)—C$_2$H$_5$ | ++ | + | +++ | + | + | +++ |
| 4-F | —nC$_6$H$_{13}$ | +++ | +++ | +++ | +++ | +++ | +++ |
| 4-Cl | —nC$_3$H$_7$ | +++ | + | ++ | +++ | + | ++ |
| 4-F | —nC$_7$H$_{15}$ | ++++ | ++ | ++++ | ++++ | + | ++++ |
| 4-Cl | —nC$_4$H$_9$ | +++ | ++ | +++ | ++ | + | ++ |
| 4-F | —nC$_8$H$_{17}$ | ++++ | +++ | ++++ | ++++ | ++ | ++++ |
| 4-Cl | —nC$_5$H$_{11}$ | +++ | ++ | ++++ | ++ | + | ++++ |
| 4-Cl | —nC$_6$H$_{13}$ | ++++ | +++ | ++++ | ++++ | ++ | ++++ |
| 2,4-(Cl)$_2$ | —C$_6$H$_{11}$ | ++++ | ++++ | ++++ | ++++ | ++++ | ++++ |
| 2-Cl | —nC$_6$H$_{13}$ | ++++ | ++++ | ++++ | ++++ | ++++ | ++++ |
| 2,4-(Cl)$_2$ | —C$_5$H$_9$ (cyclopentyl) | ++++ | +++ | ++++ | ++++ | ++ | ++++ |
| 2-Cl | —nC$_7$H$_{15}$ | ++++ | ++ | ++++ | ++++ | ++ | ++++ |
| 2-Cl | —nC$_8$H$_{17}$ | ++++ | +++ | ++++ | ++++ | ++ | ++++ |
| 2,4-(Cl)$_2$ | —CH$_2$—C$_6$H$_4$—OCH$_3$ | +++ | ++ | ++++ | ++ | ++ | ++++ |
| H | —CH$_2$—C$_6$H$_3$(Cl)(Cl) | ++++ | ++ | ++++ | ++++ | ++ | ++++ |
| 2,4-(Cl)$_2$ | —CH$_2$—C$_6$H$_4$—CH$_3$ | ++++ | ++ | ++++ | ++++ | ++ | ++++ |
| H | —CH$_2$—C$_6$H$_4$—Cl | ++ | o | ++ | + | o | ++ |

In view of the aforementioned anti-fungal and anti-bacterial activities, this invention provides valuable compositions comprising the subject imidazoles (I) or the acid addition salts thereof as the active ingredient in a solvent or a solid, semi-solid or liquid diluent or carrier, and, in addition, it provides an effective method of combating fungus or bacterial growth by use of an effective anti-fungal or anti-bacterial amount of such imidazoles (I) or salts thereof. The subject compounds can be used in suitable solvents or diluents, in the form of emulsions, suspensions, dispersions or ointments, on suitable solid or semi-solid carrier substances, in ordinary or synthetic soaps, detergents or dispersion media, if desired, together with other compounds having arachnicidal, insecticidal, ovicidal, fungicidal and/or bactericidal effects, or together with inactive additives.

Solid carrier substances which are suitable for the preparation of compositions in powder form include various inert, porous and pulverous distributing agents of inorganic or organic nature, such as, for example, tricalcium phosphate, calcium carbonate, in the form of prepared chalk or ground limestone, kaolin, bole, bentonite, talcum, kieselguhr and boric acid; powdered cork, sawdust, and other fine pulverous materials of vegetable origin are also suitable carrier substances.

The active ingredient is mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, such as pulverous preparations can also be made readily wettable with water, so that suspensions are obtained.

Inert solvents used for the production of liquid preparations should preferably not be readily inflammable and should be as far as possible odorless and as far as possible non-toxic to warm-blooded animals or plants in the relevant surroundings. Solvents suitable for this purpose are high-boiling oils, for example, of vegetable origin, and lower-boiling solvents, such as, for example, isopropanol, dimethylsulfoxide, hydrogenated napthalenes and alkylated napthalenes. It is, of course, also possible to use mixtures of solvents. Solutions can be prepared in the usual way, if necessary, with assistance of solution promotors. Other liquid forms which can be used consist of emulsions or suspensions of the active compound in water or suitable inert solvents, or also concentrates for preparing such emulsions, which can be directly adjusted to the required concentration. For this purpose, the active ingredient is, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the active component can be incorporated, if necessary, with the aid of solution promotors and/or emulsifiers. Vaseline and other cream bases are examples of semi-solid carrier substances.

Furthermore, it is possible for the active component to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combating fungi and bacteria, e.g., in closed chambers and storage rooms, and for application to vegetation for eradicating or for preventing infections by fungi or bacteria.

The subject compounds and compositions thereof can be applied by conventional methods. For example, a fungus or bacterial growth or a material to be treated or to be protected against attack by fungus or bacterium can be treated with the subject compounds and the compositions thereof by dusting, sprinkling, spraying, brushing, dipping, smearing, impregnating or other suitable means.

When the subject compounds are employed in combination with suitable carriers, e.g., in solution, suspension, dust, powder, ointment, emulsion, and the like forms, a high activity over a very high range of dilution is observed. For example, concentrations of the active ingredient ranging from 0.1 – 10 percent by weight, based on the weight of composition employed, have been found effective in combating fungi or bacteria. Of course, higher concentrations may also be employed as warranted by particular situation.

The following examples are intended to illustrate, but not to limit, the scope of the present invention. Unless otherwise stated, all parts are by weight.

EXAMPLE I

To a stirred and cooled (ice-bath) solution of 27 parts of 4-fluorobenzeneacetonitrile in 180 parts of N,N-dimethylformamide are added 6.2 parts of sodium hydride dispersion 78% and the whole is stirred for 1 hour while cooling. Then there are added dropwise 31 parts of 1-bromopentane. Upon completion, stirring is continued for 2 hours at room temperature. The reaction mixture is poured onto 1000 parts of water and the product is extracted twice with 2,2'-oxybispropane. The combined extracts are washed three times with water, dried, filtered and evaporated. The residue is distilled, yielding 21 parts of 4-fluoro-α-pentylbenzeneacetonitrile; bp. 85°–93° C at 0.1 mm. pressure.

EXAMPLE II

In a manner similar to that described in Example I the following compounds were prepared, using equivalent amounts of appropriate precursors.

α-butyl-4-fluorobenzeneacetonitrile; bp. 75°–85° C at 0.1 mm. pressure;

4-fluoro-α-hexylbenzeneacetonitrile; bp. 100°–106° C at 0.05 mm. pressure;

4-chloro-α-propylbenzeneacetonitrile; bp. 80° C at 0.01–0.05 mm. pressure;

4-fluoro-α-heptylbenzeneacetonitrile; bp. 110°–115° C at 0.05–0.1 mm. pressure;

4-fluoro-α-octylbenzeneacetonitrile; bp. 125°–130° C at 0.1 mm. pressure;

2-chloro-α-heptylbenzeneacetonitrile; bp. 120°–123° C at 0.1 mm. pressure;

2-chloro-α-hexylbenzeneacetonitrile; bp. 110°–113° C at 0.2 mm. pressure;

2,4-dichloro-α-(4-methoxyphenylmethyl)benzenepropanenitrile; mp. 76.7° C;

α-(2,4-dichlorophenyl)-4-fluorobenzenepropanenitrile; mp. 72.7° C;

α-(2,4-dichlorophenyl)benzenebutanenitrile; bp. 155°–160° C at 0.05 mm. pressure;

2-chloro-α-[3-(2-chlorophenyl)-2-propenyl]benzeneacetonitrile; bp. 180°–195° C at 0.1–0.2 mm. pressure;

2,4-dichloro-α-[3-(2-chlorophenyl)-2-propenyl]benzeneacetonitrile; mp. 89.2° C;

2,4-dichloro-α-cyclopentylbenzeneacetonitrile; bp. 115°–120° C at 0.05 mm. pressure; and
2,4-dichloro-α-cyclohexylbenzeneacetonitrile; mp. 75° C.

EXAMPLE II

In a manner similar to that described in Example I, using equivalent amounts of appropriate precursors and the indicated solvent below in place of the N,N-dimethylformamide used therein, the following compounds were prepared.

A. In dimethylsulfoxide as a solvent were prepared:

2,4-dichloro-α-(2-methylpropyl)benzeneacetonitrile; bp. 106°–108° C at 0.1 mm. pressure;
2-chloro-α-pentylbenzeneacetonitrile; bp. 104°–106° C at 0.05 mm. pressure;
2-chloro-α-butylbenzeneacetonitrile; bp. 88°–90° C at 0.05 mm. pressure;
2-chloro-α-(2-methylpropyl)benzeneacetonitrile; bp. 82°–84° C at 0.05 mm. pressure;
α-butyl-2,4-dichlorobenzeneacetonitrile; bp. 101°–104° C at 0.05 mm. pressure;
2,4-dichloro-α-pentylbenzeneacetonitrile; bp. 115° C at 0.05 mm. pressure;
2,4-dichloro-α-heptylbenzeneacetonitrile; bp. 138°–141° C at 0.2 mm. pressure;
2,4-dichloro-α-hexylbenzeneacetonitrile; bp. 129° C at 0.1 mm. pressure;
2,4-dichloro-α-octylbenzeneacetonitrile; bp. 147°–149° C at 0.1 mm. pressure;
2,4-dichloro-α-(2-methylprophy)benzeneacetonitrile; bp. 106°–108° C at 0.1 mm. pressure;
2-chloro-α-(2-propenyl)benzeneacetonitrile; bp. 74°–77° C at 0.05 mm. pressure;
2,4-dichloro-α-(2-chlorophenyl)benzenepropanenitrile; mp. 99.4° C;
2-bromo-α-(2,4-dichlorophenyl)benzenepropanenitrile; mp. 86.8° C; and
4-bromo-α-(2,4-dichlorophenyl)benzenepropanenitrile; mp. 105.1° C.

B. In hexamethylphosphoric triamide as a solvent were prepared:
2-chloro-α-(2,4-dichlorophenyl)benzenepropanenitrile; mp. 89.8° C;
4-chloro-α-(2-chlorophenyl)benzenepropanenitrile; bp. 145°–150° C at 0.05 mm. pressure;
2-chloro-α-(4-chlorophenyl)benzenepropanenitrile; mp. 74° C;
2,4-dichloro-α-(4-chlorophenyl)benzenepropanenitrile; mp. 60° C;
2-(2,4-dichlorophenyl)-3-(2,6-dichlorophenyl)propionitrile; mp. 105.1° C;
3-(p-chlorophenyl)-2-(2,4-dichlorophenyl)propionitrile; mp. 97° C; and
2,3-bis(2,4-dichlorophenyl)propionitrile; mp. 108.5° C.

C. The following were prepared using a mixture of hexamethylphosphoric triamide and benzene as a solvent:
2,4-dichloro-α-(2,6-dichlorophenyl)benzenepropanenitrile; mp. 125.7° C;
2,6-dichloro-α-(4-chlorophenylmethyl)benzeneacetonitrile; mp. 96°–97.5° C; and
2,6-dichloro-α-(4-chlorophenyl)benzenepropanenitrile; mp. 116.9° C.

D. The following were prepared by carrying out the reaction in a mixture of N,N-dimethylformamide and benzene:

4-chloro-α-pentylbenzeneacetonitrile; bp. 95°–98° C at 0.01 mm. pressure;
4-fluoro-α-propylbenzeneacetonitrile; bp. 80°–85° C at 0.4 mm. pressure;
4-chloro-α-hexylbenzeneacetonitrile; bp. 118°–124° C at 0.05 mm. pressure;
4-bromo-α-butylbenzeneacetonitrile; bp. 116°–125° C at 0.2 mm. pressure;
2,6-dichloro-α-(2-chlorophenyl)benzenepropanenitrile; mp. 110° C;
α-(2,4-dichlorophenyl)-4-methylbenzenepropanenitrile; mp. 65° C; and
α-(2,4-dichlorophenyl)benzenepropanenitrile; mp. 64.4° C.

EXAMPLE IV

A. Gaseous hydrogen chloride is introduced through 200 parts of methanol till saturation, while cooling at 0° C. Then there are added 39 parts of 2,4-dichloro-α-(2-chlorophenyl)benzenepropanenitrile and the whole is stirred and refluxed for 24 hours. The reaction mixture is poured onto water and the product is extracted twice with 2,2'-oxybispropane. The combined extracts are washed twice with water, dried, filtered and evaporated. The residue is crystallized from methanol, yielding 34.2 parts of methyl 2,4-dichloro-α-(2-chlorophenyl)-benzenepropanoate; mp. 67.9° C.

B. By repeating the foregoing procedure except that an equivalent quantity of the appropriate nitrile precursor and ethanol as a solvent are used, there is obtained ethyl 2,6-dichloro-α-(4-chlorophenyl) benzenepropanoate; mp. 83.4° C.

EXAMPLE V

In a manner similar to that described in Example IV, the following methyl ester residues were prepared from the corresponding nitriles:

methyl 4-chloro-α-(2-chlorophenyl)benzenepropanoate;
methyl 2-chloro-α-(2,4-dichlorophenyl)benzenepropanoate;
methyl 2-chloro-α-(2-chlorophenyl)benzenepropanoate;
methyl 2-bromo-α-(2,4-dichlorophenyl)benzenepropanoate;
methyl 4-bromo-α-(2,4-dichlorophenyl)benzenepropanoate;
methyl α-(2,4-dichlorophenyl)-4-methoxybenzenepropanoate;
methyl α-(2,4-dichlorophenyl)benzenepropanoate;
methyl 2,6-dichloro-α-(2-chlorophenyl)benzenepropanoate;
methyl α-(2,4-dichlorophenyl)-4-methylbenzenepropanoate;
methyl α-(2,4-dichlorophenyl)benzenebutanoate;
methyl 2-chloro-α-propylbenzeneacetate;
methyl 2-chloro-α-pentylbenzeneacetate;
methyl α-butyl-2-chlorobenzeneacetate;
methyl 2-chloro-α-(2-methylpropyl)benzeneacetate;
methyl 2,4-dichloro-α-ethylbenzeneacetate;
methyl 2,4-dichloro-α-propylbenzeneacetate;
methyl α-butyl-2,4-dichlorobenzeneacetate;
methyl 2,4-dichloro-α-pentylbenzeneacetate;

methyl 2,4-dichloro-α-heptylbenzeneacetate;
methyl 2,4-dichloro-α-hexylbenzeneacetate;
methyl 2,4-dichloro-α-octylbenzeneacetate;
methyl 2,4-dichloro-α-(2-methylpropyl)benzeneacetate;
methyl 4-fluoro-α-propylbenzeneacetate;
methyl 4-fluoro-α-pentylbenzeneacetate;
methyl α-butyl-4-fluorobenzeneacetate;
methyl 4-fluoro-α-hexylbenzeneacetate;
methyl 4-chloro-α-propylbenzeneacetate;
methyl 4-fluoro-α-heptylbenzeneacetate;
methyl 4-fluoro-α-octylbenzeneacetate;
methyl 4-chloro-α-pentylbenzeneacetate;
methyl 4-chloro-α-hexylbenzeneacetate;
methyl 2-chloro-α-hexylbenzeneacetate;
methyl 2-chloro-α-heptylbenzeneacetate;
methyl 2-chloro-α-octylbenzeneacetate;
methyl 4-bromo-α-butylbenzeneacetate;
methyl 2-chloro-α-(2-propenyl)benzeneacetate;
methyl 2,4-dichloro-α-(2-propenyl)benzeneacetate;
methyl 2-chloro-α-[3-(2-chlorophenyl)-2-propenyl]benzeneacetate;
methyl 2,4-dichloro-α-[3-(2-chlorophenyl)-2-propenyl]benzeneacetate; and
methyl α-(2,4-dichlorophenyl)-4-fluorobenzenepropanoate.

EXAMPLE VI

The following ethyl ester residues were prepared by a procedure similar to that described in Example IV, except that an equivalent amount of the appropriate precursors were used and that ethanol was used in place of the methanol used therein:

ethyl 3-(p-chlorophenyl)-2-(2,4-dichlorophenyl)propionate;
ethyl 2,3-bis(2,4-dichlorophenyl)propionate;
ethyl 2-(2,4-dichlorophenyl)-3-(2,6-dichlorophenyl)propanoate;
ethyl 2,3-bis(4-chlorophenyl)propanoate;
ethyl 2,4-dichloro-α-(4-chlorophenyl)benzenepropanoate;
ethyl 2-chloro-α-(4-chlorophenyl)benzenepropanoate;
ethyl 4-fluoro-α-methylbenzeneacetate; and
ethyl 4-chloro-α-methylbenzeneacetate.

EXAMPLE VII

A mixture of 30 parts of methyl benzeneacetate, 6.8 parts of sodium hydride dispersion 78%, 135 parts of N,N-dimethylformamide and 180 parts of benzene is stirred for 1 hour at room temperature, while nitrogen gas is introduced. Another 90 parts of benzene is added. Then there is added dropwise, during a 30 minutes-period, a solution of 43.4 parts of 1,3-dichloro-4-(chloromethyl)benzene in 45 parts of N,N-dimethylformamide. Upon completion, stirring is continued for 30 minutes at room temperature. The reaction mixture is poured onto water and the product is extracted twice with 2,2'-oxybispropane. The combined extracts are washed with water, dried, filtered and evaporated. The residue is distilled, yielding 26.5 parts of methyl 2,4-dichloro-α-phenylbenzenepropanoate; bp. 140°–145° C at 0.05 mm. pressure.

EXAMPLE VIII

In manner similar to that described in Example VII, the following compound was prepared:

methyl 2-chloro-α-phenylbenzenepropanoate; bp. 143°–150° C at 0.05 mm. pressure.

EXAMPLE IX

A mixture of 27 parts of 2,4-dichloro-α-(2,6-dichlorophenyl)benzenepropanenitrile, 27 parts of potassium hydroxide and 100 parts of 1,2-ethanediol is stirred and refluxed for 48 hours. The reaction mixture is allowed to cool to room temperature, poured onto water (800 parts) and acidified with an excess of a concentrated hydrochloric acid solution. The precipitated product is filtered off and crystallized from ethanol, yielding 18 parts of 2,4-dichloro-α-(2,6-dichlorophenyl)benzenepropanoic acid; mp. 220°–222° C.

EXAMPLE X

In a manner similar to that described in Example IX, the following carboxylic acids were prepared from an equivalent amount of the appropriate nitrile precursors:

4-chloro-α-(2,6-dichlorophenyl)benzenepropanoic acid; mp. 157.4° C;
2,4-dichloro-α-(1-methylpropyl)benzeneacetic acid as an oily residue;
2,4-dichloro-α-cyclohexylbenzeneacetic acid; mp. 154° C;
2,4-dichloro-α-cyclopentylbenzeneacetic acid; mp. 147.2° C; and
2-chloro-α-cyclohexylbenzeneacetic acid; mp. 134.1° C.

EXAMPLE XI

Gaseous hydrogen chloride is introduced through 200 parts of methanol till saturation, while cooling at 0° C. Then there are added 17 parts of 2,4-dichloro-α-(2,6-dichlorophenyl)benzenepropanoic acid and the whole is stirred and refluxed for 72 hours. The reaction mixture is poured onto water and the product is extracted twice with 1,1'-oxybisethane. The combined extracts are washed successively once with a diluted sodium bicarbonate solution and twice with water, dried, filtered and evaporated. The residue is crystallized from methanol, yielding 13.11 parts of methyl 2,4-dichloro-α-(2,6-dichlorophenyl)benzenepropanoate; mp. 115.1° C.

EXAMPLE XII

In a manner similar to that described in Example XI, the following methyl esters were prepared from an equivalent amount of the appropriate precursors:

methyl 2,4-dichloro-α-(1-methylpropyl)benzeneacetate as a residue;
methyl 4-chloro-α-(2,6-dichlorophenyl)benzenepropanoate; mp. 67.6° C;
methyl 2,4-dichloro-α-cyclohexylbenzeneacetate as a residue;
methyl 2,4-dichloro-α-cyclopentylbenzeneacetate as a residue; and
methyl 2-chloro-α-cyclohexylbenzeneacetate; mp. 58.2° C.

EXAMPLE XIII

To a stirred solution of 14.1 parts of methyl 2,4-dichloro-α-(2,6-dichlorophenyl)benzenepropanoate and 6.8 parts of lithium iodide in 120 parts of acetonitrile are added portionwise, during a 5-minutes-period, 2 parts of sodium borohydride. Upon completion, stirring is continued overnight at reflux temperature. The reaction mixture is allowed to cool to room temperature. Then there are added successively 100 parts of a concentrated hydrochloric acid solution (carefully) and after stirring for 30 minutes, 1000 parts of water. The product is extracted twice with 2,2'-oxybispropane. The combined extracts are washed twice with water, dried, filtered and evaporated, yielding 11.2 parts of 2,4-dichloro-β-(2,6-dichlorophenyl)benzenepropanol.

EXAMPLE XIV

In a manner similar to that described in Example XIII, the following compounds were prepared from an equivalent amount of the appropriate ester precursors:

4-chloro-β-(2,6-dichlorophenyl)benzenepropanol;
2,4-dichloro-β-(p-chlorobenzyl)phenethylalcohol;
2,3-bis(2,4-dichlorophenyl)-1-propanol;
2,6-dichloro-β-(2,4-dichlorophenyl)benzenepropanol;
2,3-bis(4-chlorophenyl)-1-propanol;
2,4-dichloro-α-(4-chlorophenyl)benzenepropanol;
2-chloro-β-(4-chlorophenyl)benzenepropanol;
2,6-dichloro-β-(4-chlorophenyl)benzenepropanol;
2,4-dichloro-β-(2-chlorophenyl)benzenepropanol;
4-chloro-β-(2-chlorophenyl)benzenepropanol; mp. 79.6° C;
β-(2,4-dichlorophenyl)-4-fluorobenzenepropanol;
β-(2,4-dichlorophenyl)-4-methoxybenzenepropanol;
4-bromo-α-(2,4-dichlorophenyl)benzenepropanol;
2-bromo-β-(2,4-dichlorophenyl)benzenepropanol; bp. 185°-193° C at 0.05 mm. pressure;
2,6-dichloro-β-(2chlorophenyl)benzenepropanol; mp. 76.9° C;
4-chloro-β-phenylbenzenepropanol;
2,4-dichloro-β-phenylbenzenepropanol;
2-chloro-β-phenylbenzenepropanol;
β-(2,4-dichlorophenyl)-4-methylbenzenepropanol;
β-(2,4-dichlorophenyl)benzenepropanol;
β-(2,4-dichlorophenyl)benzenebutanol;
4-fluoro-β-methylbenzeneethanol; bp. 61°-63° C at 0.1 mm. pressure;
4-chloro-α-methylbenzeneethanol; bp. 76°-78° C at 0.1 mm. pressure;
2-chloro-β-propylbenzeneethanol; bp. 88°-90° C at 0.1 mm. pressure;
2-chloro-β-pentylbenzeneethanol; bp. 100°-105° C at 0.05 mm. pressure;
β-butyl-2-chlorobenzeneethanol;
2-chloro-β-(2-methylpropyl)benzeneethanol; bp. 86°-88° C at 0.05 mm. pressure;
2,4-dichloro-β-(2-methylpropyl)benzeneethanol; bp. 118°-122° C at 0.2 mm. pressure;
4-fluoro-β-propylbenzeneethanol; bp. 80°-85° C at 0.1-0.2 mm. pressure;
4-fluoro-β-pentylbenzeneethanol; bp. 87°-92° C at 0.05 mm. pressure;
β-butyl-4-fluorobenzeneethanol; bp, 80°-85° C at 0.05 mm. pressure;
4-chloro-β-pentylbenzeneethanol as a residue;
4-fluoro-β-octylbenzeneethanol; bp. 115° C at 0.01 mm. pressure;
4-fluoro-β-heptylbenzeneethanol; bp. 103°-107° C at 0.01 mm. pressure;
4-chloro-β-propylbenzeneethanol; bp. 85° C at 0.01 mm. pressure;
4-fluoro-β-hexylbenzeneethanol; bp. 99°-100° C at 0.05 mm. pressure;
4-chloro-β-hexylbenzeneethanol; bp. 115°-120° C at 0.05 mm. pressure;
4-bromo-β-butylbenzeneethanol;
2-chloro-β-octylbenzeneethanol;
2-chloro-β-heptylbenzeneethanol;
2-chloro-β-hexylbenzeneethanol;
2,4-dichloro-β-(1-methylpropyl)benzeneethanol;
2-chloro-β-(2-propenyl)benzeneethanol; bp. 85°-88° C at 0.1 mm. pressure;
2,4-dichloro-β-(2-propenyl)benzeneethanol; bp. 115-116° C at 0.1 mm. pressure;
2,4-dichloro-β-[3-(2-chlorophenyl)-2-propenyl]benzeneethanol;
2-chloro-β-[3-(2-chlorophenyl)-2-propenyl]benzeneethanol;
2,4-dichloro-β-cyclohexylbenzeneethanol;
2-chloro-β-cyclohexylbenzeneethanol; and
2,4-dichloro-β-cyclopentylbenzeneethanol.

EXAMPLE XV

The following compounds were prepared by operations similar to that described in Example XIII using the indicated lithium salt and the indicated solvent, from an equivalent amount of the appropriate ester precursor:

A. With lithium chloride in acetonitrile as a solvent was prepared:

2,4-dichloro-β-propylbenzeneethanol;

B. With a mixture of lithium chloride and lithium iodide in acetonitrile was prepared:

2,4-dichloro-β-ethylbenzeneethanol;

C. With lithium chloride in a mixture of acetonitrile and N,N-dimethylformamide were prepared:

2-chloro-β-(2,4-dichlorophenyl)benzenepropanol;
2-chloro-β-(2-chlorophenyl)benzenepropanol;
β-butyl-2,4-dichlorobenzeneethanol; bp. 118°-121° C at 0.1 mm. pressure;
2,4-dichloro-β-pentylbenzeneethanol;
2,4-dichloro-β-heptylbenzeneethanol; bp. 146°-149° C at 0.1 mm. pressure;
2,4-dichloro-β-hexylbenzeneethanol; bp. 140°-142° C at 0.1 mm. pressure; and
2,4-dichloro-β-octylbenzeneethanol; bp. 150°-153° C at 0.05-0.1 mm. pressure.

EXAMPLE XVI

A. To a stirred solution of 48.2 parts of 2,3-bis(2,4-dichlorophenyl)-1-propanol in 150 parts of pyridine are added dropwise 14 parts of mesyl chloride at room temperature. Upon completion, stirring at room temperature is continued overnight. The reaction mixture is poured onto water and the product is extracted twice with diisopropylether. The combined extracts are washed successively three times with a dilute hydrochloride acid solution and once with water, dried, filtered and evaporated. The residue is crystallized first from methanol and then from diisopropylether, yielding 25.8 parts of 2,3-bis(2,4-dichlorophenyl)-1-propanol methanesulfonate; mp. 84° C.

B. By repeating the foregoing procedure, except that an equivalent quantity of the appropriate alcohol precursor was used, there is obtained:

β-cyclohexylbenzeneethanol methanesulfonate; mp. 78.8° C;
2-chloro-β-cyclohexylbenzeneethanol methanesulfonate; mp. 67° C;
4-chloro-β-(2,6-dichlorophenyl)benzenepropanol methanesulfonate; mp. 72° C; and
2,6-dichloro-β-(4-chlorophenyl)benzenepropanol methanesulfonate; mp. 155° C.

EXAMPLE XVII

In a manner similar to that described in Example XVI, the following methanesulfonate residues were prepared, from an equivalent amount of the appropriate alcohol:

2,4-dichloro-β-(2,6-dichlorophenyl)benzenepropanol methanesulfonate;
2-chloro-β-(2,4-dichlorophenyl)benzenepropanol methanesulfonate;
2,4-dichloro-β-(p-chlorobenzyl)phenethylalcohol methanesulfonate ester;
2,6-dichloro-β-(2,4-dichlorophenyl)benzenepropanol methanesulfonate;
2,3-bis(4-chlorophenyl)-1-propanol methanesulfonate;
2,4-dichloro-α-(4-chlorophenyl)benzenepropanol methanesulfonate;
2-chloro-β-(4-chlorophenyl)benzenepropanol methanesulfonate;
2,4-dichloro-β-(2-chlorophenyl)benzenepropanol methanesulfonate;
4-chloro-β-(2-chlorophenyl)benzenepropanol methanesulfonate,
2-chloro-β-(2-chlorophenyl)benzenepropanol methanesulfonate;
4-fluoro-β-methylbenzeneethanol methanesulfonate;
4-chloro-α-methylbenzeneethanol methanesulfonate;
2-chloro-β-propylbenzeneethanol methanesulfonate;
2-chloro-β-pentylbenzeneethanol methanesulfonate;
β-butyl-2-chlorobenzeneethanol methanesulfonate;
2-chloro-β-(2-methylpropyl)benzeneethanol methanesulfonate;
2,4-dichloro-β-ethylbenzeneethanol methanesulfonate;
2,4-dichloro-β-propylbenzeneethanol methanesulfonate;
β-butyl-2,4-dichlorobenzeneethanol methanesulfonate;
2,4-dichloro-β-pentylbenzeneethanol methanesulfonate;
2,4-dichloro-β-heptylbenzeneethanol methanesulfonate;
2,4-dichloro-β-hexylbenzeneethanol methanesulfonate;
2,4-dichloro-β-octylbenzeneethanol methanesulfonate;
2,4-dichloro-β-(2-methylpropyl)benzeneethanol methanesulfonate;
4-fluoro-β-propylbenzeneethanol methanesulfonate;
4-fluoro-β-pentylbenzeneethanol methanesulfonate;
β-butyl-4-fluorobenzeneethanol methanesulfonate;
4-fluoro-β-hexylbenzeneethanol methanesulfonate;
2,4-dichloro-β-(1-methylpropyl)benzeneethanol methanesulfonate;
4-chloro-β-propylbenzeneethanol methanesulfonate;
4-fluoro-β-heptylbenzeneethanol methanesulfonate;
β-butyl-4-chlorobenzeneethanol methanesulfonate;
4-fluoro-β-octylbenzeneethanol methanesulfonate;
4-chloro-β-pentylbenzeneethanol methanesulfonate;
4-chloro-β-hexylbenzeneethanol methanesulfonate;
4-bromo-β-butylbenzeneethanol methanesulfonate;
2-chloro-β-octylbenzeneethanol methanesulfonate;
2-chloro-β-heptylbenzeneethanol methanesulfonate;
2-chloro-β-hexylbenzeneethanol methanesulfonate;
2-chloro-β-(2-propenyl)benzeneethanol methanesulfonate;
2,4-dichloro-(β-(2-propenyl)benzeneethanol methanesulfonate;
2,4-dichloro-β-[3-(2-chlorophenyl)-2-propenyl]benzeneethanol methanesulfonate;
2-chloro-β-[3-(2-chlorophenyl)-2-propenyl]benzeneethanol methanesulfonate;
2,4-dichloro-β-cyclopentylbenzeneethanol methanesulfonate; and
2,4-dichloro-β-cyclohexylbenzeneethanol methanesulfonate.

EXAMPLE XVIII

The following methanesulfonate residues were prepared from an equivalent amount of the appropriate alcohol precursor, in similar operations as described in Example XVI, using however a mixture of pyridine and 2,2'-oxybispropane as a reaction medium:

2-bromo-β-(2,4-dichlorophenyl)benzenepropanol methanesulfonate;
4-bromo-β-(2,4-dichlorophenyl)benzenepropanol methanesulfonate;
β-(2,4-dichlorophenyl)-4-methoxybenzenepropanol methanesulfonate;
β-(2,4-dichlorophenyl)-4-fluorobenzenepropanol methanesulfonate;
2,6-dichloro-β-(2-chlorophenyl)benzenepropanol methanesulfonate;
4-chloro-β-phenylbenzenepropanol methanesulfonate;
2,4-dichloro-β-phenylbenzenepropanol methanesulfonate;
2-chloro-β-phenylbenzenepropanol methanesulfonate;
β-(2,4-dichlorophenyl)-4-methylbenzenepropanol methanesulfonate; and
β-(2,4-dichlorophenyl)benzenebutanol methanesulfonate.

EXAMPLE XIX

A mixture of 6.8 parts of imidazole, 8.6 parts of 2,3-bis(2,4-dichlorophenyl)-1-propanol methanesulfonate and 150 parts of dimethylformamide is stirred and refluxed overnight. The reaction mixture is allowed to cool to room temperature, poured onto water and the product is extracted twice with diisopropylether. The combined extracts are washed twice with water and acidified with an excess of a concentrated nitric acid solution. The nitrate salt is filtered off and crystallized from a mixture of 2-propanol and diisopropylether, yielding 5.2 parts of 1-[2,3-bis(2,4-dichlorophenyl)-propyl]imidazole nitrate; mp. 147.3° C.

EXAMPLE XX

The procedure of Example XIX was repeated except that the 2,3-bis(2,4-dichlorophenyl)-1-propanol methanesulfonate was replaced by an equivalent amount of an appropriate methanesulfonate ester to obtain the following compounds:

1-[2-(2,4-dichlorophenyl)-3-(2,6-dichlorophenyl)-propyl]-1H-imidazole nitrate; mp. 161° C.
1-[β-(p-chlorobenzyl)-2,4-dichlorophenethyl]-imidazole nitrate; mp. 150.7° C.

1-[2-(2-chlorophenyl)-3-(2,6-dichlorophenyl)propyl]-1H-imidazole nitrate; mp. 180.1° C.
1-[3-(4-chlorophenyl)-2-phenylpropyl]-1H-imidazole nitrate; mp. 129.6° C;
1-[3-(2,4-dichlorophenyl)-2-phenylpropyl]-1H-imidazole nitrate; mp. 154.6° C.
1-[3-2(-chlorophenyl)-2-phenylpropyl]-1H-imidazole nitrate; mp. 167.1° C;
1-[2-(2,4-dichlorophenyl)-3-(4-methylphenyl)propyl]-1H-imidazole nitrate; mp. 158.6° C; and
1-[2-(2,4-dichlorophenyl)-3-phenylpropyl]-1H-imidazole nitrate; mp. 146.7° C.

EXAMPLE XXI

A mixture of 27.2 parts of 1H-imidazole, 19.5 parts of 2,4-dichloro-β-(4-chlorophenyl)benzenepropanol methanesulfonate, 4 parts of potassium iodide and 150 parts of N,N-dimethylformamide is stirred and refluxed overnight. The reaction mixture is poured onto water and the product is extracted twice with 2,2'-oxybispropane. The combined extracts are washed twice with water and an excess of a concentrated nitric acid solution is added. The nitrate salt is filtered off and crystallized from 4-methyl-2-pentanone, yielding 6.3 parts of 1-[2-(4-chlorophenyl)-3-(2,4-dichlorophenyl) propyl]-1H-imidazole nitrate; mp. 143.7° C.

EXAMPLE XXII

By repeating the procedure of example XXI and using an equivalent amount of an appropriate methanesulfonate ester in place of the 2,4-dichloro-β-(4-chlorophenyl)benzenepropanol methanesulfonate used therein, the following compounds were prepared:

1-[3-(2,4-dichlorophenyl)-2-(2,6-dichlorophenyl)-propyl]-1H-imidazole nitrate; mp. 191.1° C;
1-[3-(4-chlorophenyl)-2-(2,6-dichlorophenyl)propyl]-1H-imidazole nitrate; mp. 138° C.
1-[2-(2,4-dichlorophenyl)-3-(4-fluorophenyl)propyl]-1H-imidazole nitrate; mp. 143.6° C;
1-[2-(2,4-dichlorophenyl)-3-(4-methoxyphenyl)-propyl]-1H-imidazole nitrate; mp. 147.7° C;
1-[3-(4-bromophenyl)-2-(2,4-dichlorophenyl)propyl]-1H-imidazole nitrate; mp. 150.5° C;
1-[3-(2-bromophenyl)-2-(2,4-dichlorophenyl)propyl]-1H-imidazole nitrate; mp. 160.8° C;
1-[2,3-bis(2-chlorophenyl)propyl]-1H-imidazole nitrate; mp. 149.9° C;
1-[3-(2-chlorophenyl)-2-(2,4-dichlorophenyl)propyl]-1H-imidazole nitrate; mp. 156.1° C;
1-[2-(2-chlorophenyl)-3-(4-chlorophenyl)propyl]-1H-imidazole nitrate; mp. 127.6° C;
1-[2-(2-chlorophenyl)-3-(2,4-dichlorophenyl)propyl]-1H-imidazole nitrate; mp. 142.7° C;
1-[2-(4-chlorophenyl)-3-(2,6-dichlorophenyl)propyl]-1H-imidazole nitrate; mp. 171.2° C;
1-[3-(2-chlorophenyl)-2-(4-chlorophenyl)propyl]-1H-imidazole nitrate; mp. 139°–141° C;
1-[2,3-bis(4-chlorophenyl)propyl]-1H-imidazole nitrate; mp. 126.9° C; and
1-[2-(2,4-dichlorophenyl)-4-phenylbutyl]-1H-imidazole nitrate; mp. 136.7° C.

EXAMPLE XXIII

A mixture of 20 parts of 1H-imidazole, 19 parts of 2-chloro-β-hexylbenzeneethanol methanesulfonate and 180 parts of N,N-dimethylformamide is stirred and refluxed overnight. The reaction mixture is cooled and poured onto water. The product is extracted three times with trichloromethane. The combined extracts are washed three times with water and stirred with silicagel. The latter is filtered off and the filtrate is evaporated. The residue is converted into the ethanedioate salt in 2-propanol and 2,2'-oxybispropane. The salt is filtered off and crystallized from a mixture of 2-propanol and 2,2'-oxybispropane, yielding 11.1 parts of 1-[2-(2-chlorophenyl)octyl]-1H-imidazole ethanedioate; mp. 133° C.

EXAMPLE XXIV

A mixture of 13 parts of 1H-imidazole, 12.5 parts of 2-chloro-β-heptylbenzeneethanol methanesulfonate and 225 parts of N,N-dimethylformamide is stirred and refluxed overnight. The reaction mixture is cooled, poured onto water and the product is extracted three times with trichloromethane. The combined extracts are washed three times with water and stirred with silicagel. The latter is filtered, off and the filtrate is evaporated. The residue is converted into the ethanedioate salt in 2-propanol and 2,2'-oxybispropane. The salt is filtered off and crystallized from a mixture of 2-propanol and 2,2'-oxybispropane, yielding 4.1 parts of 1-[2-(2-chlorophenyl)nonyl]-1H-imidazole ethanedioate; mp. 134.2° C.

EXAMPLE XXV

A mixture of 22 parts of 1H-imidazole, 23.6 parts of 2,4-dichloro-β-heptylbenzeneethanol methanesulfonate and 180 parts of N,N-dimethylformamide is stirred and refluxed overnight. After cooling, the reaction mixture is poured onto 500 parts of water and the product is extracted three times with trichloromethane. The combined extracts are washed three times with water and stirred with silicagel for 1 hour. The latter is filtered off and the filtrate is evaporated. The residue is converted into the nitrate salt in 2,2'-oxybispropane. The salt is filtered off and crystallized from a mixture of 4-methyl-2-pentanone and 2,2'-oxybispropane, yielding 10 parts of 1-[2-(2,4-dichlorophenyl)nonyl]-1H-imidazole nitrate; mp. 91.2° C.

EXAMPLE XXVI

By repeating the procedure of Example XXV and using an equivalent amount of an appropriate methanesulfonate ester in place of the 2,4-dichloro-β-heptylbenzeneethanol methanesulfonate used therein, the following compounds were prepared:

1-[2-(4-fluorophenyl)propyl]-1H-imidazole nitrate mp. 91.5° C;
1-[2-(4-chlorophenyl)propyl]-1H-imidazole nitrate; mp. 81.2° C;
1-[2-(2-chlorophenyl)pentyl]-1H-imidazole nitrate; mp. 101.4° C;
1-[2-(2-chlorophenyl)heptyl]-1H-imidazole nitrate; mp. 86.9° C;
1-[2-(2-chlorophenyl)hexyl]-1H-imidazole nitrate; mp. 118.8° C;
1-[2-(4-chlorophenyl)octyl]-1H-imidazole nitrate; mp. 122° C;
1-[2-(2-chlorophenyl)-4-methylpentyl]-1H-imidazole nitrate; mp. 165.5° C;
1-[2-(2,4-dichlorophenyl)butyl]-1H-imidazole nitrate; mp. 121.1° C;
1-[2-(2,4-dichlorophenyl)pentyl]-1H-imidazole; mp. 142.5° C;

1-[2-(2,4-dichlorophenyl)hexyl]-1H-imidazole nitrate; mp. 140 °C;

1-[2-(2,4-dichlorophenyl)heptyl]-1H-imidazole nitrate mp. 116.7 °C;

1-[2-(2,4-dichlorophenyl)octyl]-1H-imidazole nitrate; mp. 90.7 °C;

1-[2-(2,4-dichlorophenyl)decyl]-1H-imidazole nitrate; mp. 82.9° C;

1-[2-(2,4-dichlorophenyl)-4-methylpentyl]-1H-imidazole nitrate; mp. 148.8° C;

1-[2-(4-fluorophenyl)pentyl]-1H-imidazole nitrate; mp. 108.3° C;

1-[2-(4-fluorophenyl)heptyl]-1H-imidazole nitrate; mp. 130° C;

1-[2-(4-fluorophenyl)hexyl]-1H-imidazole nitrate; mp. 112.6° C;

1-[2-(4-fluorophenyl)octyl]-1H-imidazole nitrate; mp. 123.5° C;

1-[2-(4-chlorophenyl)pentyl]-1H-imidazole nitrate mp. 118° C;

1-[2-(4-fluorophenyl)nonyl]-1H-imidazole nitrate; mp. 110.1° C;

1-[2-(4-chlorophenyl)hexyl]-1H-imidazole nitrate; mp. 96.1° C;

1-[2-(4-fluorophenyl)decyl]-1H-imidazole nitrate; mp. 118.8° C;

1-[2-(4-chlorophenyl)heptyl]-1H-imidazole nitrate; mp. 116° C;

1-[2-(2,4-dichlorophenyl)-3-methylpentyl]-1H-imidazole nitrate; mp. 160.6° C;

1-[2-(2-chlorophenyl)decyl]-1H-imidazole nitrate; mp. 70.3° C; and

1-[2-(4-bromophenyl)hexyl]-1H-imidazole nitrate; mp. 113.4° C.

EXAMPLE XXVII

A mixture of 13.4 parts of 1H-imidazole; 10 parts of 2-chloro-β-(2-propenyl)benzeneethanol methanesulfonate and 90 parts of N,N-dimethylformamide is stirred and refluxed overnight. After cooling, the reaction mixture is poured onto 500 parts of water. The product is extracted three times with trichloromethane. The combined extracts are washed three times with water, dried, filtered and evaporated. The product is converted into the nitrate salt in a mixture of 2-propanol and 2,2'-oxybispropane (activated charcoal), yielding 2.6 parts of 1-[2-(2-chlorophenyl)-4-pentenyl]-1H-imidazole nitrate; mp. 88.6° C.

EXAMPLE XXVIII

A mixture of 27 parts 1H-imidazole, 25 parts of 2,4-dichloro-β-(2-propenyl)benzeneethanol methanesulfonate and 180 parts of N,N-dimethylformamide is stirred and refluxed overnight. The reaction mixture is cooled and poured onto 500 parts of water. The product is extracted three times with trichloromethane. The combined extracts are washed twice with water and stirred with silicagel. The latter is filtered off and the filtrate is evaporated. The residue is converted into the nitrate salt in 2,2'-oxybispropane. The salt is filtered off and crystallized from a mixture of 2-propanol and 2,2'-oxybispropane, yielding 14 parts of 1-[2-(2,4-dichlorophenyl)-4-pentenyl]-1H-imidazole nitrate; mp. 112.6° C.

EXAMPLE XXIX

A mixture of 20 parts of 1H-imidazole, 25 parts of 2,4-dichloro-β-[3-(2-chlorophenyl)-2-propenyl]benzeneethanol methanesulfonate and 180 parts of N,N-dimethylformamide is stirred and refluxed overnight. The reaction mixture is cooled, poured onto 500 parts of water and the product is extracted three times with trichloromethane. The combined extracts are washed three times with water and stirred with silicagel. The latter is filtered off and the filtrate is evaporated. The residue is converted into the nitrate salt in 2,2'-oxybispropane. The salt is filtered off and crystallized from a mixture of 2-propanol and 2,2'-oxybispropane, yielding 12.2 parts of 1-[5-(2-chlorophenyl)-2-(2,4-dichlorophenyl)-4-pentenyl]-1H-imidazole nitrate; mp. 110.3° C.

EXAMPLE XXX

A mixture of 34 parts of 1H-imidazole, 39 parts of 2-chloro-β-[3-(2-chlorophenyl)-2-propenyl]benzeneethanol methane-sulfonate and 180 parts of N,N-dimethylformamide is stirred and refluxed overnight. After cooling, the reaction mixture is poured onto 500 parts of water and the product is extracted three times with trichloromethane. The combined extracts are washed twice with water and stirred with silicagel. The latter is filtered off and the filtrate is evaporated. The residue is converted into the nitrate salt in 2,2'-oxybispropane. The salt is precipitated as an oil. The supernatant phase is decanted. The oily salt is dissolved in 4-methyl-2-pentanone. The solution is saturated with 2,2'-oxybispropane at room temperature. After cooling overnight at 0° C, the solid product is precipitated. It is filtered off, washed successively with 4-methyl2-pentanone and 2,2'-oxybispropane, and dried, yielding 17.1 parts of 1-[2,5-bis(2-chlorophenyl)-4-pentenyl]-1H-imidazole nitrate; mp. 92.4° C.

EXAMPLE XXXI

A mixture of 18 parts of 1H-imidazole, 18 parts of 2,4-dichloro-β-cyclopentylbenzeneethanol methane-sulfonate and 225 parts of N,N-dimethylformamide is stirred and refluxed overnight. The reaction mixture is cooled and poured onto water. The product is extracted three times with trichloromethane. The combined extracts are washed three times with water and stirred with silicagel. The latter is filtered off and the filtrate is evaporated. The residue is crystallized from petroleumether. The product is filtered off and recrystallized from a mixture of 2,2'-oxybispropane and petroleum-ether, yielding 6.8 parts of 1-[2-cyclopentyl-2-(2,4-dichlorophenyl)-ethyl]-1H-imidazole; mp. 97.6° C.

EXAMPLE XXXII

A mixture of 18.5 parts of 1H-imidazole, 19.5 parts of 2,4-dichloro-β-cyclohexylbenzeneethanol methane-sulfonate and 225 parts of N,N-dimethylformamide is stirred and refluxed overnight. The reaction mixture is cooled, poured onto water and the product is extracted three times with trichloromethane. The combined extracts are washed three times with water and stirred with silicagel. The latter is filtered off and the filtrate is evaporated. The residue is converted into the nitrate salt in 2,2'-oxybispropane. The salt is filtered off and crystallized from a mixture of 2-propanol and 2,2'-oxybispropane, yielding 10.8 parts of 1-[2-cyclohexyl-2-(2,4-dichlorophenyl)ethyl]-1H-imidazole nitrate; mp. 199.3° C.

EXAMPLE XXXIII

A mixture of 18 parts of 1H-imidazole, 17 parts of 2-chloro-β-cyclohexylbenzeneethanol methanesulfonate and 225 parts of N,N-dimethylformamide is stirred and refluxed overnight. The reaction mixture is cooled and poured onto water. The product is extracted three times with trichloromethane. The combined extracts are washed three times with water and stirred with silicagel. The latter is filtered off and the filtrate is evaporated. The residue is converted into the nitrate salt in 2,2'-oxybispropane. The salt is filtered off and crystallized from a mixture of 2-propanol and 2,2'-oxybispropane. It is filtered off again and recrystallized from 2-propanol, yielding 8.2 parts of 1-[2-(2-chlorophenyl)-2-cyclohexylethyl]-1H-imidazole nitrate; mp. 203.6° C.

EXAMPLE XXXIV

A mixture of 17 parts of 1H-imidazole, 14.3 parts of β-cyclohexylbenzeneethanol methanesulfonate and 180 parts of N,N-dimethylformamide is stirred and refluxed overnight. After cooling, the reaction mixture is poured onto 500 parts of water and the product is extracted three times with trichloromethane. The combined extracts are washed three times with water and stirred with silicagel. The latter is filtered off and the filtrate is evaporated. The residue is converted into the nitrate salt in 2,2'-oxybispropane. The salt is filtered off and crystallized from a mixture of 2-propanol and 2,2'-oxybispropane, yielding 8.8 parts of 1-(2-cyclohexyl-2-phenylethyl)-1H-imidazole nitrate; mp. 162.2° C.

EXAMPLE XXXV

By repeating the procedure of Example XIX and using an equivalent amount of an appropriate β-R-arylethanol methane-sulfonate in place of the 2,3-bis(2,4-dichlorophenyl)-1-propanol methanesulfonate used therein, the following compounds are obtained in the form of a nitrate salt:

1-[3-(2-chlorophenyl)-2-(4-methylphenyl)propyl]-1H-imidazole;
1-[3-(2-chlorophenyl)-2-(4-methoxyphenyl)propyl]-1H-imidazole;
1-[3-(2-chlorophenyl)-2-(2-methylphenyl)propyl]-1H-imidazole;
1-[3-(2-chlorophenyl)-2-(2-methoxyphenyl)propyl]-1H-imidazole;
1-[3-(2-chlorophenyl)-2-(4-nitrophenyl)propyl]-1H-imidazole;
1-[3-(2-chlorophenyl)-2-(3-nitrophenyl)propyl]-1H-imidazole;
4-[1-(2-chlorophenylmethyl)-2-(1H-imidazol-1-yl)ethyl]benzonitrile;
1-{3-(2-chlorophenyl)-2-[4-(trifluoromethyl)phenyl]propyl}-1H-imidazole;
1-[2-(4-methylphenyl)hexyl]-1H-imidazole;
1-[2-(2-methylphenyl)hexyl]-1H-imidazole;
1-[2-(4-methoxyphenyl)hexyl]-1H-imidazole;
1-[2-(2-methoxyphenyl)hexyl]-1H-imidazole;
1-[2-(4-nitrophenyl)hexyl]-1H-imidazole;
1-[2-(3-nitrophenyl)hexyl]-1H-imidazole;
1-{2-[4-(trifluoromethyl)phenyl]hexyl}-1H-imidazole;
1-[2-(2,4-dichlorophenyl)-3-(4-nitrophenyl)propyl]-1H-imidazole;
1-{2-(2,4-dichlorophenyl)-3-[4-(trifluoromethyl)phenyl]}-1H-imidazole; and
4-[2-(2,4-dichlorophenyl)-3-(1H-imidazol-1-yl)propyl]-benzonitrile.

EXAMPLE XXXVI

The compositions according to this invention are employed in those forms which are customarily used for fungus or bacteria control, for example, as suspensions, dusting powders, solutions, ointments and the like. The following will further illustrate the invention, the parts being parts by weight unless otherwise specified:

| (1) SUSPENSION: | |
| --- | --- |
| 1 kg. | 1-[3-(2-chlorophenyl)-2-(2,4-dichlorophenyl)-propyl]1H-imidazole nitrate |
| 2 l. | technical xylene |
| 350 ml. | surface active agent. |
| Water | dilute to desired concentration of active ingredient |

The 1-[3-(2-chlorophenyl)-2-(2,4-dichlorophenyl)-propyl]-1H-imidazole nitrate forms a stable aqueous suspension when dissolved in the xylene and emulsified by means of the surface active agent.

2. DUSTING POWDER: 20 Parts of 1-[2-(2,4-dichlorophenyl) hexyl]-1H-imidazole nitrate are ground with 360 parts of talcum in a ball mill, then 8 parts of olein are added and grinding is continued, and finally the mixture is mixed with 4 parts of slaked lime. The powder which is formed can be sprayed satisfactorily and has good adhesive power. It can be used for dusting or for plant protection purposes.

3. SOLUTION: 5 Parts of 1-[3-(2-chlorophenyl)-2-(2,4-dichlorophenyl)propyl]-1H-imidazole nitrate are dissolved in 95 parts of alkylated naphthalene and used as a spray for the treatment of fungus-infected subjects or on walls, floors or other objects to prevent infection by fungi.

4. OINTMENT: 10 Parts of 1-[3-(2-chlorophenyl)-2-(2,4-dichlorophenyl)propyl]-1H-imidazole nitrate are dissolved in a warm, liquefied mixture of 400 parts of polyethylene glycol 400 and 590 parts of polyethylene glycol 1500. The solution is stirred during cooling, and used as an ointment for treatment against fungi and bacteria.

EXAMPLE XXXVII

A mixture of 15.8 parts of β-(2,4-dichlorophenyl)-benzene-propanol, 12.15 parts of methanesulfonyl chloride, 50 parts of pyridine and 70 parts of 2,2'-oxybispropane is stirred overnight at room temperature. The reaction mixture is poured onto water and the product is extracted twice with 2,2'-oxybispropane. The combined extracts are washed twice with a diluted hydrochloric acid solution and once with water, dried, filtered and evaporated. The residue is triturated in methanol. The product is filtered off and crystallized from ethanol, yielding 7.28 parts of β-(2,4-dichlorophenyl)benzenepropanol methanesulfonate; mp. 87.3° C.

We claim:
1. A composition for deterring the growth of a microorganism selected from the group consisting of fungus and bacterium comprising an inert carrier material and as an active ingredient an antimicrobially effective amount of a compound selected from the group consisting of an imidazole derivative having the formula:

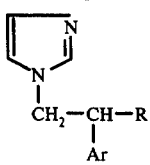

and the therapeutically active non-toxic acid addition salts thereof, wherein:
Ar is a member selected from the group consisting of phenyl, mono-, di- and trihalophenyl, loweralkylphenyl, loweralkyloxyphenyl, nitrophenyl, cyanophenyl and trifluoromethylphenyl; and
R is a member selected from the group consisting of alkyl having from 1 to 10 carbons, cycloalkyl having from 3 to 6 carbon atoms, lower alkenyl, aryl-loweralkyl, aryl-loweralkenyl, said aryl being a member selected from the group consisting of phenyl, mono-, di- and tri-halophenyl, loweralkylphenyl, loweralkyloxyphenyl, nitrophenyl, cyanophenyl and trifluoromethylphenyl.

2. A composition for deterring the growth of a microorganism selected from the group consisting of fungus and bacterium comprising an inert carrier material and as an active ingredient an antimicrobially effective amount of 1-[2-(2,4-dichlorophenyl)hexyl]-1H-imidazole or the therapeutically active acid addition salts thereof.

3. A composition for deterring the growth of a microorganism selected from the group consisting of fungus and bacterium comprising an inert carrier material and as an active ingredient an antimicrobially effective amount of 1-[2-(2,4-dichlorophenyl)decyl]-1H-imidazole or the therapeutically active acid addition salts thereof.

4. A composition for deterring the growth of a microorganism selected from the group consisting of fungus and bacterium comprising an inert carrier material and as an active ingredient an antimicrobially effective amount of 1-[2-(2,4-dichlorophenyl)-4-methylpentyl]-1H-imidazole or the therapeutically active acid addition salts thereof.

5. A composition for deterring the growth of a microorganism selected from the group consisting of fungus and bacterium comprising an inert carrier material and as an active ingredient an antimicrobially effective amount of 1-[3-(2-chlorophenyl)-2-(2,4-dichlorophenyl)propyl]-1H-imidazole or the therapeutically active acid addition salts thereof.

6. A composition for deterring the growth of a microorganism selected from the group consisting of fungus and bacterium comprising an inert carrier material and as an active ingredient an antimicrobially effective amount of 1-(2-cyclohexyl-2-phenylethyl)-1H-imidazole or the therapeutically active acid addition salts thereof.

7. A composition for deterring the growth of a microorganism selected from the group consisting of fungus and bacterium comprising an inert carrier material and as an active ingredient an antimicrobially effective amount of 1-[2-(2-chlorophenyl)-octyl]-1H-imidazole or the therapeutically active acid addition salts thereof.

8. The method of deterring the growth of a microorganism selected from the group consisting of fungus and bacterium which comprises subjecting said microorganism to the action of an antimicrobially effective amount of a compound selected from the group consisting of an imidazole derivative having the formula:

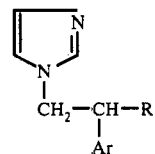

and the therapeutically active non-toxic acid addition salts thereof, wherein:
Ar is a member selected from the group consisting of phenyl, mono-, di- and trihalophenyl, loweralkylphenyl, loweralkyloxyphenyl, nitrophenyl, cyanophenyl and trifluoromethylphenyl; and
R is a member selected from the group consisting of alkyl, having from 1 to 10 carbon atoms, cycloalkyl, having from 3 to 6 carbon atoms, lower alkenyl, aryl-loweralkyl, aryl-loweralkenyl, said aryl being a member selected from the group consisting of phenyl, mono-, di- and trihalophenyl, loweralkylphenyl, loweralkyloxyphenyl, nitrophenyl, cyanophenyl and trifluoromethylphenyl.

9. The method of deterring the growth of a microorganism selected from the group consisting of fungus and bacterium which comprises subjecting said microorganism to the action of an antimicrobially effective amount of 1-[2-(2,4-dichlorophenyl)hexyl]-1H-imidazole or the therapeutically active acid addition salts thereof.

10. The method of deterring the growth of a microorganism selected from the group consisting of fungus and bacterium which comprises subjecting said microorganism to the action of an antimicrobially effective amount of 1-[2-(2,4-dichlorophenyl)decyl]-1H-imidazole or the therapeutically active acid addition salts thereof.

11. The method of deterring the growth of a microorganism selected from the group consisting of fungus and bacterium which comprises subjecting said microorganism to the action of an antimicrobially effective amount of 1-[2-(2,4-dichlorophenyl)-4-methylpentyl]-1H-imidazole or the therapeutically active acid addition salts thereof.

12. The method of deterring the growth of a microorganism selected from the group consisting of fungus and bacterium which comprises subjecting said microorganism to the action of an antimicrobially effective amount of 1-[3-(2-chlorophenyl)-2-(2,4-dichlorophenyl)propyl]-1H-imidazole or the therapeutically active acid addition salts thereof.

13. The method of deterring the growth of a microorganism selected from the group consisting of fungus and bacterium which comprises subjecting said microorganism to the action of an antimicrobially effective amount of 1-(2-cyclohexyl-2-phenylethyl)-1-H-imidazole or the therapeutically active acid addition salts thereof.

14. The method of deterring the growth of a microorganism selected from the group consisting of fungus and bacterium which comprises subjecting said microorganism to the action of an antimicrobially effective amount of 1-[2-(2-chlorophenyl)-octyl]-1H-imidazole or the therapeutically active acid addition salts thereof.

* * * * *

Notice of Adverse Decision in Interference

In Interference No. 99,965, involving Patent No. 3,991,201, J. Heeres, L. J. J. Backx, and J. H. Mostmans, 1(-β-ARYL-β-R-ETHYL) IMIDAZOLES AS ANTIMICROBIAL AGENTS, final judgment adverse to the patentees was rendered June 29, 1979, as to claims 1 and 8.

[*Official Gazette September 4, 1979.*]

UNITED STATES PATENT AND TRADEMARK OFFICE
CERTIFICATE OF CORRECTION

PATENT NO. : 3,991,201
DATED : Nov. 9, 1976
INVENTOR(S) : Heeres et al.

It is certified that error appears in the above-identified patent and that said Letters Patent are hereby corrected as shown below:

In Column 6, Table A, under heading $\text{Sap.}_{(11)}$, line 13, there should be a ++

In Column 8, Table A-continued, under heading $\text{Sap.}_{(11)}$, line 10, there should be a +

In Column 10, Table A-continued, under heading $\text{Sap.}_{(11)}$, line 2, there should be a ++

In Column 10, Table A-continued, under heading $\text{Sap.}_{(11)}$, line 13, there should be a ++

In Column 19, line 59, "C." should be omitted

In Column 30, line 33, "4-methyl2-" should read "4-methyl-2-"

Signed and Sealed this

Twenty-second Day of January 1980

[SEAL]

Attest:

SIDNEY A. DIAMOND

Attesting Officer

Commissioner of Patents and Trademarks